United States Patent [19]

Coward

[11] Patent Number: 5,772,982
[45] Date of Patent: Jun. 30, 1998

[54] METHOD OF USING HYALURONIC ACID FOR THE DETECTION, LOCATION AND DIAGNOSIS OF TUMORS

[76] Inventor: Roderick T. Coward, 1365 Milton Avenue, Mississauga, Ontario, Canada, L5G 3C5

[21] Appl. No.: 732,171

[22] Filed: Oct. 16, 1996

Related U.S. Application Data

[63] Continuation of Ser. No. 288,052, Aug. 10, 1994, abandoned.

[51] Int. Cl.[6] .......................... A61K 51/00; A61M 36/14
[52] U.S. Cl. ........................ 424/1.73; 424/9.6; 424/1.11; 424/9.1
[58] Field of Search .................................. 424/1.11, 1.65, 424/1.73, 9.1, 9.3, 9.4, 9.5, 9.6, 488, 1.37; 536/1.11, 123.1; 514/54; 534/7, 10–16

[56] References Cited

U.S. PATENT DOCUMENTS

| | | | |
|---|---|---|---|
| 3,852,413 | 12/1974 | Cammarata | 424/1.11 |
| 4,303,676 | 12/1981 | Balazs | 424/359 |
| 4,784,991 | 11/1988 | Nimrod et al. | 514/62 |
| 4,925,678 | 5/1990 | Ranney | 424/493 |
| 5,019,498 | 5/1991 | Chichibu | 435/7.5 |
| 5,128,326 | 7/1992 | Balazs et al. | 514/54 |

FOREIGN PATENT DOCUMENTS

| | | |
|---|---|---|
| 1303984 | 6/1992 | Canada. |
| 0 138 572 | 4/1985 | European Pat. Off.. |
| WO 9 316 732 | 9/1993 | WIPO. |
| WO 9 316 733 | 9/1993 | WIPO. |

OTHER PUBLICATIONS

West (1989), Experimental Cell Research, vol. 183, pp. 179–196, "The Effect of Hyaluronate and Its Oligosaccharides on Endothelial Cell Proliferation and Monolayer Integrity."

Alho et al., (1989), J. Cell. Biology, vol. 108, pp. 1557–1565, "The Hyaluronate Receptor Is Preferentially Expressed on Proliferating Epithelial Cells".

Atul C. Mehta et al., "Photosensitizers as Diagnostics and Therapeutic Tools in Oncology", *Cancer Management in Man: Detection, Diagnosis, Surgery, Radiology, Chronobiology, Endocrine Therapy*, A.L. Goldson (ed.), pp. 220–225 (1989).

T. Frebourg et al., "Serum Hyaluronate in Malignant Pleural Mesothelioma", *Cancer*, vol. 59, No. 12, pp. 2104–2107 (Jun. 15, 1987). (Journal Abstract).

N. Mangakis et al., "Determining the Degree of Malignancy of Individual Cases of Mammary Carcinoma on the Basis of Clinical, Morphological and Biochemical Parameters", *Bull. Cancer*, vol. 77, No. 3, pp. 235–242 (1990). (Journal Abstract).

T.C. Laurent et al., "The Properties and Turnover of Hyaluronan", *Ciba Found Symp*, vol. 124, pp. 9–29 (1986). (Journal Abstract).

K. Hobarth et al., "Topical Chemoprophylaxis of Superficial Bladder Cancer with Mitomycin C and Adjuvant Hyaluronidase", *Eur Urol*, vol. 21, No. 3, pp. 206–210 (1992). (Journal Abstract).

D.P. De Klerk, "The Glycosaminoglycans of Human Bladder Cancers of Varying Grade and Stage", *J. Urol*, vol. 134, No. 5, pp. 978–981 (Nov. 1985). (Journal Abstract).

D.P. De Klerk et al., "Glycosaminoglycans of Human Prostatic Cancer", *J Urol*, vol. 131, No. 5, pp. 1008–1112 (May 1984). (Journal Abstract).

*Primary Examiner*—John Kight
*Assistant Examiner*—Dameron Jones
*Attorney, Agent, or Firm*—Gary M. Nath; Karen L. Orzechowski; Nath & Associates

[57] ABSTRACT

A method for detecting, locating and diagnosing tumors by labeling hyaluronic acid with a diagnostic agent, administering the labelled hyaluronic acid compound to a patient, and utilizing an appropriate imaging method to detect said labelled hyaluronic acid compound in or on the patient.

11 Claims, No Drawings

METHOD OF USING HYALURONIC ACID FOR THE DETECTION, LOCATION AND DIAGNOSIS OF TUMORS

This application is a continuation application of U.S. patent application Ser. No. 08/288,052, filed Aug. 10, 1994, now abandoned, the entire contents of which are hereby incorporated in their entirety.

BACKGROUND OF THE INVENTION

1. Field of the Invention

The present invention pertains to a method for detecting, locating and diagnosing tumors utilizing hyaluronic acid. In particular, the invention is directed to the use of hyaluronic acid labelled with a diagnostic agent for the detection, location and diagnosis of tumors.

2. Description of the Related Art

Hyaluronic acid (hereinafter referred to as "HA") is a naturally occurring high viscosity glycosaminoglycan comprising 250 to 25,000 disaccharide units linked by alternating $\beta(1-3)$ glucuronidic and $\beta(1-4)$ glucosaminidic bonds. The anionic character of its glucuronic acid residues causes HA to bind cations such as $K^+$, $Na^+$ and $Ca^{2+}$ tightly. Although HA is a linear molecule, it adopts a random coil configuration in solution and in physiological media, with the extent of the coiling dependent upon the concentration of HA, the range of molecular weights of the constituent HA polymers, and their degree of entanglement. It is found in all animal tissues, most notably the skin, the synovial fluids within the joints, and the vitreous humor of the eyes in humans. HA occurs as a free polysaccharide, aggregated with other molecules, or bound to plasma membranes. It is found in abundance in extracellular matrices whenever rapid cell proliferation occurs, as is the case in cancer cells.

HA is characterized by hydrophilic regions having the ability to attract and absorb water, as well as a hydrophobic region. This affinity for water, as well as HA's outstanding safety record, has made it popular with cosmetic companies who use HA in the production of moisturizing creams and other personal appearance products to increase the moisture in the upper layer of the skin, thus increasing its softness and flexibility. U.S. Pat. No. 4,303,676 to Balazs discloses various cosmetic formulations based on HA.

As a result of its biological properties, HA is known to play a critical role in a wide variety of biologically significant processes, including wound healing, cell division, cell migration and differentiation, and in facilitating the movement of ions and metabolites between the cells. HA receptors and HA binding proteins have been found to be present in large amounts at sites of a number of disease states, all of which are associated with cell proliferation, infiltration or migration.

HA is often known to be present at elevated levels in the blood of patients with cancer and other diseases. Utilizing this knowledge, methods for quantitative determination of HA in the blood utilizing radioimmunoassays and enzymoimmunologic assays have been developed which can be used for diagnosis of these diseases. U.S. Pat. No. 5,019,498 to Chichibu discloses one such method, and Boutin et al. disclose another in *Serum hyaluronate in malignant pleural mesothelioma*, 59 Cancer (1987), 2104–2107. In addition, the ratio of HA to certain other glycosaminoglycans has been used as a means of defining the degree of malignancy of certain cancers, including breast, bladder and prostate cancers. Mangakis et al., *Determining the degree of malignancy of individual cases of mammary carcinoma on the basis of clinical, morphological and biochemical parameters*, 77 Bull. Cancer (Paris) (1990), 235–242; DeKlerk, *The glycosaminoglycans of human bladder cancers of varying grade and stage*, 134 J. Urol. (1985), 978–981; DeKlerk et al.; *Glycosaminoglycans of human prostatic cancer*, 131 J. Urol. (1984), 1008–1012. However, these methods can only detect the existence or, in some cases, the extent of disease, not its specific location or identity.

HA is used as a carrier molecule to target pain and cancer cell killing drugs to cancerous sites in humans, because the random coil configuration that HA adopts in solution creates a "net" capable of entrapping a wide variety of drug compounds, with the rate of release depending on the size and solubility characteristics of the drug and the relative pore size of the net. HA's affinity for water is instrumental in its ability to act as a carrier molecule to target the drugs, because sites of tumors have a higher than normal concentration of water. It has been observed, using HA labelled with tritium, that HA concentrates at the site of tumors, penetrating their deep cores. Klein et al., *Hyaluronic acid enhances tritiated fluorouracil uptake in experimental cancer*, 1st International Workshop on Hyaluronon in Drug Delivery (1993), 11–15. Using this knowledge, HA has been combined with medicinal chemicals and administered to patients. The HA concentrates at the sites of tumors and is able to carry the drugs into the dense cores of the cancerous tumors, increasing their effectiveness. For example, administration of HA in combination with mitomycin C to patients with superficial bladder cancer was found to decrease the number of recurring tumors compared to patients treated with mitomycin alone. Hobarth et al., *Topical chemoprophylaxis of superficial bladder cancer with mitomycin C and adjuvant hyaluronidase*, 2,1 Eur. Urol. (1992), 206–210. WO Publication No. 9316733 discloses an anticancer composition containing HA or derivatives thereof for topical application onto skin or other exposed tissue.

As a result of this targeted action, the drugs are more effective against the tumors to which they are targeted. In addition, they work primarily against the tumors to which they are targeted and less against normal and healthy parts of the body. Consequently, smaller doses or lesser concentrations of the drugs than are used in conventional therapy may be administered and still be effective, and the side effects of the drugs will be thus reduced since they are targeted and can be administered in lower quantities.

Early diagnosis of malignant tumors, or neoplasms, is of great importance. Malignant tumors grow rapidly. The neoplastic cells invade and destroy adjacent normal tissue, interrupting vital functions and causing bleeding when they invade blood vessels. They can metastasize (i.e., generate independent tumor nodules) through lymphatic channels or blood vessels to other tissues in the body, continuing the sequence of tumor growth in the new locations. Diagnosis and treatment in the earliest stages can prevent this outcome, thus decreasing mortality and decreasing health care costs. In addition, early diagnosis can allow less radical treatments to be utilized, making treatment less risky and less traumatic for the patient.

Determining the precise location of the tumor in the body is of particular importance. The site of the tumor is relevant to various aspects of the clinical course of the disease, including the likelihood and route of metastatic spread, the effect of the tumor on bodily functions, and the type of treatment which can be utilized. Current methods of detection and diagnosis include biopsy, mammogram, mediastinoscopy, laparotomy, laparoscopy, needle aspiration, bronchoscopy, barium swallow or enema, esophagoscopy, gastroscopy, cholangiography, peritoneoscopy, ultrasound, radioisotope scan and CT scan. Unfortunately, these methods are often difficult, unreliable, expensive, uncomfortable or even dangerous for the patient.

Tumor immunodiagnosis is a non-invasive method for diagnosing cancer based on the knowledge that most tumors release antigenic macromolecules that can be detected in the blood or other body fluid of the patient by immunoassay. These antigenic macromolecules, known as tumor markers, include carcinoembryonic antigen (CEA), α-fetoprotein (AFP), β-subunit of human chorionic gonadotropin (β-HCG), and prostate specific antigen (PSA). However, while detection of one of these markers may indicate that a patient has a tumor associated with that marker, it does not indicate the specific location of the tumor.

SUMMARY OF THE INVENTION

The present invention is directed to a method for detecting, locating and/or diagnosing tumors in a mammal, utilizing hyaluronic acid labelled with a diagnostic agent.

In a preferred embodiment, the invention involves labelling medical grade hyaluronic acid or its salts, homologs, analogs, derivatives, complexes, esters or subunits with an isotope; administering an appropriate amount of the labelled HA in a pharmaceutically appropriate carrier to the mammal; after time sufficient for the labelled hyaluronic acid to penetrate the tumor, utilizing an appropriate imaging device to detect the labelled hyaluronic acid in the body of the mammal; and diagnosing the identity of the tumor based on the location, shape and size of the region of concentrated labelled hyaluronic acid in the body of the mammal.

In another preferred embodiment, the invention involves labelling medical grade hyaluronic acid or its salts, homologs, analogs, derivatives, complexes, esters or subunits with a fluorescent dye; administering an appropriate amount of the labelled hyaluronic acid in a pharmaceutically appropriate carrier to the mammal; exposing the target area to light of an appropriate wavelength; after time sufficient for the labelled hyaluronic acid to penetrate the tumor, visually inspecting the target area to detect the labelled hyaluronic acid in or on the body of the mammal; and diagnosing the identity of the tumor based on the location, shape and size of the region of concentrated labelled hyaluronic acid in or on the body of the mammal.

DETAILED DESCRIPTION OF THE INVENTION

As discussed above, previous investigations of HA have been directed to use in cosmetics and for treating tumors and other dysfunctions. The technology of the present invention presents for the first time an effective method of using HA or one of its salts, homologs, analogs, derivatives, complexes, esters or subunits combined with a diagnostic agent to detect tumors. This combined or converted HA will hereinafter be referred to as "diagnostic HA".

The HA can be labelled with a diagnostic agent using any appropriate methods. For example, HA can be chemically linked to a radioactive isotope or other diagnostic agent. Alternatively, HA can be physically mixed with the diagnostic agent in a solution with the HA. The coiling effect of the HA will surround the diagnostic agent in a "net." The excess (non-surrounded) diagnostic agent is then removed and the HA administered.

HA's properties will cause the diagnostic HA to target tumor cells. The diagnostic HA will accumulate at the tumor sites when administered to a patient and can then be detected and/or imaged using appropriate medical detection and/or imaging devices, which will allow the exact location of tumors to be determined more readily than other diagnostic methods. Knowing the anatomic site of a tumor is of great importance in determining the type of treatment to be employed and enabling the physician to treat the tumor to prevent further growth and metastasis.

Radioactive isotopes are particularly useful as diagnostic agents in the claimed method. They emit electromagnetic radiation as gamma rays, which can be detected, localized and quantitated from outside the body even when administered in minute quantities. They also emit positrons, which can be detected using positron emission tomography (PET). Techniques for detecting isotopes in the body include scintigraphy, such as gamma camera scintigraphy; nuclear magnetic resonance imaging (MRI); tomography, including computerized tomography (CT), PET, and single photon emission computed tomography (SPECT); and various forms of radiography including mammography, xeroradiography, cerebral arteriography, angiography, digital subtraction angiography and iodine K-edge dichromography.

Any radioactive isotope with sufficient energy levels to be detected can be used with the claimed method. Preferred isotopes include americium-241, barium-137 (particularly in barium sulfate), calcium-47 (particularly in calcium chloride), cesium-137 (particularly in cesium sulfate and cesium chloride), chromium-51 (particularly in sodium chromate, chromium disodium edetate, or chromic chloride), cobalt-60 and cobalt-57 (in their metallic form or in vitamin $B_{12}$), copper-64 (particularly in copper versenate), fluorine-18 (particularly in sodium fluoride), gallium-67 (particularly in gallium citrate), colloidal gold-198, colloidal indium-113m, indium-ill (particularly in indium chloride), iodine-123 and iodine-125 (particularly in sodium iodide and iodohippurate sodium), iodine-131 (particularly in sodium iodide, diiodofluorescein, iodohippurate sodium, sodium diatrizoate, iodopyracet, diatrizoate methyl glucamine, sodium diprotrizoate, sodium acetrizoate, or sodium iothalamate), iridium-192, iron-55 and iron-59 (particularly in ferrous citrate, ferrous sulfate and ferric chloride), krypton-85 gas, lead-210, mercury-197 and mercury-203 (particularly in chlormerodrin), phosphorus-32 (particularly in sodium phosphate), potassium-42 (particularly in potassium carbonate), radium-226, ruthenium-106, selenium-75 (particularly in selenomethionine), sodium-24 (particularly in sodium chloride), strontium--85 and strontium-87m (particularly in strontium nitrate or strontium chloride), sulfur-35 (particularly in sodium sulfate), technetium-99m (particularly in pertechnetate, technetium DTPA, technetium stannous polyphosphate, technetium stannous etidronate or colloidal technetium sulfate), thallium-201 (particularly in thallous chloride), tritium, xenon-133 gas, and ytterbium-169 (particularly in ytterbium-DTPA). In addition, naturally occurring elements that are constituents of organic matter, including carbon, oxygen and nitrogen, can be made radioactive and thus capable of detection using PET. Stable isotopes such as carbon-13, phosphorous-13, boron-11 and fluorine-19 can be used for MRI.

Another type of diagnostic agent that is appropriate for use in the claimed method is a fluorescent dye. When chemically linked to HA, administered and exposed to light of an appropriate wavelength, it will appear fluorescent in the region of the tumor. This is particularly useful in detecting and diagnosing skin cancers and oral cancers.

Examples of fluorescent dyes which can be used to label HA include fluorescein, which appears bright green when exposed to ultraviolet (UV) light; auramine O, which appears yellow when exposed to UV light; and hematoporphyrin and rhodamine B, which appear red upon exposure to UV light. Tumors inside the body can be exposed to light and visualized with this method by utilizing a fiberoptic scope. Image intensifiers and wavelength detectors may be necessary to intensify the image, particularly for small tumors.

Tumors suitable for detection utilizing the claimed method include colonic adenocarcinomas, lung cancers (including squamous cell carcinoma, small- and large-cell undifferentiated carcinomas and adenocarcinomas), kidney cancers, uterine and cervical cancers, prostate cancer, bladder cancer, ovarian cancer, esophageal cancers, liver cancers (including hepatocarcinomas), pancreatic cancer, stomach cancer, liposarcoma, synovial sarcoma, rhabdomyosarcoma, chondrosarcoma, osteosarcoma, Ewing's tumor, testicular and ovarian dysgerminoma, retinoblastoma, Wilms' tumor, neuroblastoma, malignant melanoma, mesothelioma, Gardner's syndrome, basal cell carcinoma, breast cancers (including adenocarcinomas and medullary carcinomas), lymphoma, medulloblastoma, choriocarcinoma, Paget's disease, multiple myeloma, glioblastoma, Burkitt's lymphoma and Kaposi's sarcoma. These examples are meant to be illustrative only and not to limit the scope of the claims in any way.

Diagnostic HA can be administered to the patient using any suitable means known to those skilled in the art, depending on the area of the body to be studied and the type of imaging method to be used. Among these methods of administration are: topical application, rectal administration, oral administration, intravenous or intraarterial injection, injection into a synovial membrane, subcutaneous or intramuscular injection, interstitial or intraperitoneal injection, or by inhalation.

The use of diagnostic HA offers a number of advantages over present methods. Among these are:

(1) earlier and more accurate detection of tumors due to enhanced imaging, particularly in cases of multiple and smaller sites that might otherwise go undetected using conventional diagnostic methods;

(2) more effective monitoring of the progression or regression of a tumor in the body;

(3) greater versatility, because diagnostic HA can utilize isotopes that can concentrate at a number of sites, rather than currently used radioactive isotopes that are capable of functioning in only specific locations or sites within the body.

The following examples illustrate but do not limit the scope of the invention:

EXAMPLE 1

This example demonstrates a method for locating a tumor in a mammal using HA labelled with a radioactive isotope. The procedure involves:

(a) complexing HA with $^{99m}$Tc-labeled stannous polyphosphate to form diagnostic HA;

(b) intravenously injecting into the patient a quantity of the diagnostic HA sufficient for a dosage of 1–4 millicuries; and (c) after about 3 hours, obtaining images under a scintillation camera equipped with a high resolution or medium resolution collimator.

EXAMPLE 2

This example demonstrates the method for locating a tumor in a mammal using HA labelled with a fluorescent dye. The procedure involves:

(a) complexing HA with dihematoporphyrin ether to form diagnostic HA;

(b) intravenously injecting the diagnostic HA into the patient over several minutes, at a dosage of about 2 mg/kg of body weight;

(c) after about 48 hours, exposing target areas to light using a krypton ion laser at 405 nm transmitted via a 400$\mu$m thin flexible quartz filament; and (d) screening for fluorescence.

The invention being thus described, it will be obvious that the same may be varied in many ways. Such variations are not to be regarded as a departure from the spirit and scope of the invention and all such modifications are intended to be included within the scope of the claims.

What is claimed is:

1. A method for detecting and locating a tumor in a mammal, comprising the steps of:

labelling hyaluronic acid or its potassium, sodium or calcium salts with a diagnostic agent;

administering said labelled hyaluronic acid to said mammal; and utilizing an appropriate imaging method to detect and locate said labelled hyaluronic acid in the body of said mammal.

2. The method of claim 1 wherein said diagnostic agent is an isotope.

3. The method of claim 2 wherein said labelled hyaluronic acid is administered utilizing a method selected from the group consisting of: rectal administration, oral administrations, injection into a vein, injection into an artery, injection into a synovial membrane, intramuscular injection, subcutaneous injection, interstitial injection, intraperitoneal injection and inhalation.

4. A method for detecting and locating a tumor in a mammal, comprising the steps of:

labelling hyaluronic acid or its potassium, sodium, or calcium salts with a fluorescent dye;

administering said labelled hyaluronic acid to said mammal; and exposing a portion of said mammal to light of an appropriate wavelength to detect and locate said labelled hyaluronic acid in the body of said mammal.

5. The method of claim 4 wherein said labelled hyaluronic acid is administered utilizing a method selected from the group consisting of: rectal administration, oral administration, injection into a vein, injection into an artery, injection into a synovial membrane, intramuscular injection, subcutaneous injection, interstitial injection, intraperitoneal injection and inhalation.

6. A method for diagnosing a tumor in a mammal, comprising the steps of:

labelling hyaluronic acid or its potassium, sodium or calcium salts with a diagnostic agent;

administering said labelled hyaluronic acid to said mammal;

utilizing an appropriate imaging method to detect and locate said labelled hyaluronic acid in the body of said mammal; and diagnosing the identity of the tumor based on the location, shape and size of the region of concentrated labelled hyaluronic acid in the body of the mammal.

7. The method of claim 6 wherein said diagnostic agent is an isotope.

8. The method of claim 7 wherein said labelled hyaluronic acid is administered utilizing a method selected from the group consisting of: rectal administration, oral administration, injection into a vein, injection into an artery, injection into a synovial membrane, intramuscular injection, subcutaneous injection, interstitial injection, intraperitoneal injection and inhalation.

9. A method for diagnosing a tumor in a mammal comprising the steps of:

labelling hyaluronic acid or its potassium, sodium, or calcium salts with a fluorescent dye;

administering said labelled hyaluronic acid to said mammal;

exposing a portion of said mammal to light of an appropriate wavelength to detect and locate said labelled hyaluronic acid in the body of said mammal; and diagnosing the identity of the tumor based on the location, shape, and size of the region of concentrated labelled hyaluronic acid in the body of the mammal.

10. The method of claim 9 wherein said labelled hyaluronic acid is administered utilizing a method selected from the group consisting of: rectal administration, oral administration, injection into a vein, injection into an artery, injection into a synovial membrane, intramuscular injection, subcutaneous injection, interstitial injection, intraperitoneal injection and inhalation.

11. A method for identifying a tumor in a mammal using diagnostic hyaluronic acid, wherein the tumor expresses an HA receptor and the diagnostic hyaluronic acid is labelled medical grade hyaluronic acid having a molecular weight of less than about 750,000 Daltons and labelled with a diagnostic agent selected from the group consisting of radioactive isotopes and fluorescent dyes, the method comprising the steps of:

administering the diagnostic hyaluronic acid to the mammal; and detecting the diagnostic hyaluronic acid in the mammal.

* * * * *